United States Patent
von Schuckmann (12) 
(10) Patent No.: US 6,189,739 B1
(45) Date of Patent: Feb. 20, 2001

(54) PUMP DISPENSER WITH THRESHOLD ACTUATION AND RESTORING SPRING

(75) Inventor: Alfred von Schuckmann, Kevelaer (DE)

(73) Assignee: AstraZeneca AB, Södertälje (SE)

( * ) Notice: Under 35 U.S.C. 154(b), the term of this patent shall be extended for 0 days.

(21) Appl. No.: 09/194,530

(22) PCT Filed: May 28, 1997

(86) PCT No.: PCT/EP97/02785

§ 371 Date: Nov. 27, 1998

§ 102(e) Date: Nov. 27, 1998

(87) PCT Pub. No.: WO97/46324

PCT Pub. Date: Dec. 11, 1997

(30) Foreign Application Priority Data

Jun. 1, 1996 (DE) ............................. 196 22 124

(51) Int. Cl.[7] .................................................. B67D 5/06
(52) U.S. Cl. ................. 222/182; 222/321.6; 222/340; 222/464.1
(58) Field of Search ........................... 222/182, 321.2, 222/321.6, 321.7, 340, 341, 464.1

(56) References Cited

U.S. PATENT DOCUMENTS

| | | | |
|---|---|---|---|
| 4,083,476 | 4/1978 | Schwartz | 222/321 |
| 5,181,658 | 1/1993 | Behar | 239/493 |
| 5,224,471 | 7/1993 | Marellie et al. | 128/200.14 |
| 5,316,198 | * 5/1994 | Fuchs et al. | 222/321.6 |
| 5,331,954 | 7/1994 | Rex et al. | 128/200.22 |
| 5,351,863 | * 10/1994 | Cecil et al. | 222/340 |
| 5,439,177 | * 8/1995 | Graf et al. | 222/321.6 |
| 5,492,248 | * 2/1996 | Ortner | 222/182 |
| 5,655,689 | * 8/1997 | Fuchs et al. | 222/321.2 |

FOREIGN PATENT DOCUMENTS

| | | |
|---|---|---|
| 195 33 979 | 3/1997 | (DE) . |
| 0407276 | 1/1991 | (EP) . |
| 0452728 | 10/1991 | (EP) . |
| 0471610 | 2/1992 | (EP) . |
| 0516472 | 12/1992 | (EP) . |
| 0679443 | 11/1995 | (EP) . |
| 2518658 | 6/1983 | (FR) . |
| 2014233 | 8/1979 | (GB) . |
| 2162594 | 2/1986 | (GB) . |
| 2262138 | 6/1993 | (GB) . |
| 8901365 | 2/1989 | (WO) . |
| 9115303 | 10/1991 | (WO) . |

* cited by examiner

*Primary Examiner*—Joseph A. Kaufman
(74) *Attorney, Agent, or Firm*—Martin A. Faber

(57) ABSTRACT

A device (G) for dispensing liquids (1), especially medicinal liquids, from a mouthpiece aperture (2), the latter being connected to a supply of liquid, by manual actuation of a piston-cylinder device (4) which allows the manual actuation only after an overload threshold (Ü) has been exceeded. The device achieves a design which is advantageous for use, and provides a powerful jet of liquid, by a smaller restoring spring force, assigned to the overload threshold (Ü), of the piston-cylinder device (4) designed as a pump (P).

23 Claims, 10 Drawing Sheets

PUMP DISPENSER WITH THRESHOLD ACTUATION AND RESTORING SPRING

FIELD AND BACKGROUND OF THE INVENTION

The invention relates to a device for dispensing liquids, especially medicinal liquids, from a mouthpiece aperture, the latter being connected to a supply of liquid, by manual actuation of a piston-cylinder device which allows the manual actuation only after an overload threshold has been exceeded.

A device of this kind is known from GB-2 262 138 A. It serves for the nasal application of a pharmaceutical liquid substance. The manual actuation system provides for the displacement of a liquid-containing cylinder of a piston-cylinder device in the direction of the mouthpiece aperture. During this process, the piston strikes against a counter abutment and is pierced by a cannula projecting freely from the counter abutment in the opposite direction to the actuating stroke. The cannula functions as a conduit leading to the mouthpiece aperture, which is designed as a single-hole nozzle. The cylinder is in the form of a cartridge containing a single portion. It can be inserted into the piston-cylinder device. A sleeve closed at the end is the support for the cartridge. This sleeve is united to the housing of the device and is held engaged in a defined stand-by position. Only after an overload threshold formed in this way has been exceeded is manual actuation allowed. The overload threshold is obtained by means of knobs on the outer wall which engage in a corresponding latching groove on spring fingers of the housing. A safeguard against unintentional actuation is thereby achieved, and this effect is completed by spacing feet of this device on the housing which extend like a protective palisade around the actuation end of the sleeve, which is configured as a slider. The catch overcome in both directions: on the one hand to bring about the dispensing piston stroke; on the other hand for the charging of the device, i.e. insertion of the disposable cartridge.

A manually actuated pump-type atomizer is revealed, for example, by GB-2 014 233 A.

SUMMARY OF THE INVENTION

It is the object of the invention to design a device of the generic type in a way which is advantageous for handling and use while providing a powerful jet of liquid.

Such a configuration provides a device of the introductory-mentioned type of increased utility. The jet is more stable and is dispensed with greater power, thus reaching the target location, e.g. the nasal cavity, even in the more remote areas. This is achieved by a smaller restoring spring force, assigned to the overload threshold, of the piston-cylinder device designed as a pump. The corresponding release interlock can be overcome only in an abrupt manner. The liquid is not simply expelled. Rather, an effect which goes beyond the action of the safeguard against unintentional actuation is achieved. Only when a certain actuating pressure has been built up by the user does the catch effect break down. The significantly lower restoring-spring spring force has virtually no impeding effect. It does not part the device but brings about the return of the pump into its initial position, at the same time drawing in and preparing the next portion. This automatic reloading creates the basis for the repeated dispensing of individual portions from the supply of liquid.

An advantageous feature of the invention is obtained if the pump piston, which is connected by means of a riser to a liquid reservoir and is configured as an intake passage, is configured as a component which is fixed relative to the liquid reservoir, the pump cylinder, which is spring-loaded in the restoring direction, has at its free end the mouthpiece aperture, on the rear side of which an insert which deflects the jet of liquid several times by means of transverse channels on the top side is arranged. It is thus possible to manage with a small number of components, the insert being allocated the function of the distributor, via the transverse channels of which, which are situated on the top side, the flow leaves the hole-type nozzle of the mouthpiece aperture in concentrated form. The likewise abrupt emergence which occurs there leads to atomization of the liquid into a very fine droplet structure and accordingly to the achievement of the spray cone desired. Such an insert occupies the volume behind the mouthpiece. This prevents or considerably reduces by simple means the collection of partial quantities of the liquid separated from the supply. The insert also fulfils a further advantageous function in that, together with a foot plate, it forms a valve element, here that of an outlet valve. It suffices if the foot plate can be bent up elastically in the edge region out of its flat extension. It is expedient if this region ends in a lip, allowing the main body or core of the insert to be used as a supporting part which is still sufficiently solid in itself. It furthermore proves to be advantageous that the transverse channels are arranged open on the top side of the cylindrical insert, around which liquid can flow, and are aligned slightly eccentrically, forming a central swirl chamber underneath the mouthpiece aperture. These measures too have a favorable effect in terms of production and also have a positive effect on the formation of the jet. The part having the mouthpiece aperture can serve as a channel cover. Furthermore, it is proposed that the insert is held by a cantilever from the wall of the pump cylinder, said wall being extended in the direction of the mouthpiece aperture. This measure ensures an additional reduction in the number of device components. In addition, an advantageous configuration is achieved by means of a pressure balance path between the supply and the pump. The falling proportion of liquid in the supply chamber is thus balanced with respect to the atmosphere. It is favorable here for the pressure balance path to be controlled by a lip which rises under negative pressure. Said lip only rises if the negative pressure is sufficiently pronounced. In contrast, when the handle of the device is located in the initial position, the pressure balance path remains closed. This avoids leakages. Another, likewise advantageous possibility is then provided in that the pressure balance path is controlled via a relative movement of the piston-cylinder device. This is achieved, by structurally straightforward means, in that the pump piston is assigned a second piston which, via a cylinder-side annular space, connects the pressure balance path, by way of a shaft and a radial passage, to the annular space, which can be manually displaced into the region of an air-passage opening. It has also proved advantageous here for the second piston to have a hole which connects an annular space and radial passage.

BRIEF DESCRIPTION OF THE DRAWINGS

With the above and other objects and advantages in view, the present invention will become more clearly understood in connection with the detailed description of preferred embodiments, when considered with the accompanying drawings of which

DETAILED DESCRIPTION OF THE PREFERRED EMBODIMENTS

The region I containing the dispenser mechanism begins, at the application end, with a mouthpiece aperture 2, directly or indirectly formed on a cylinder 3.

The cylinder 3 is part of a piston-cylinder device 4 forming the heart of a pump P. The pump chamber of this pump bears the reference 5. A piston 6 runs therein.

The end section of the pump chamber 5 facing the mouthpiece aperture 2 forms a transverse wall 7. There is a central opening in the latter. The corresponding hole is denoted 8. The latter continues on the top side of the transverse wall 7 into an intermediate chamber 9. The inside diameter of the latter corresponds essentially to that of the pump chamber 5. The upper rim of the chamber forms a valve-seating surface 10 for an outlet valve V1 of the pump P, said outlet valve interacting with it.

Figure 1:
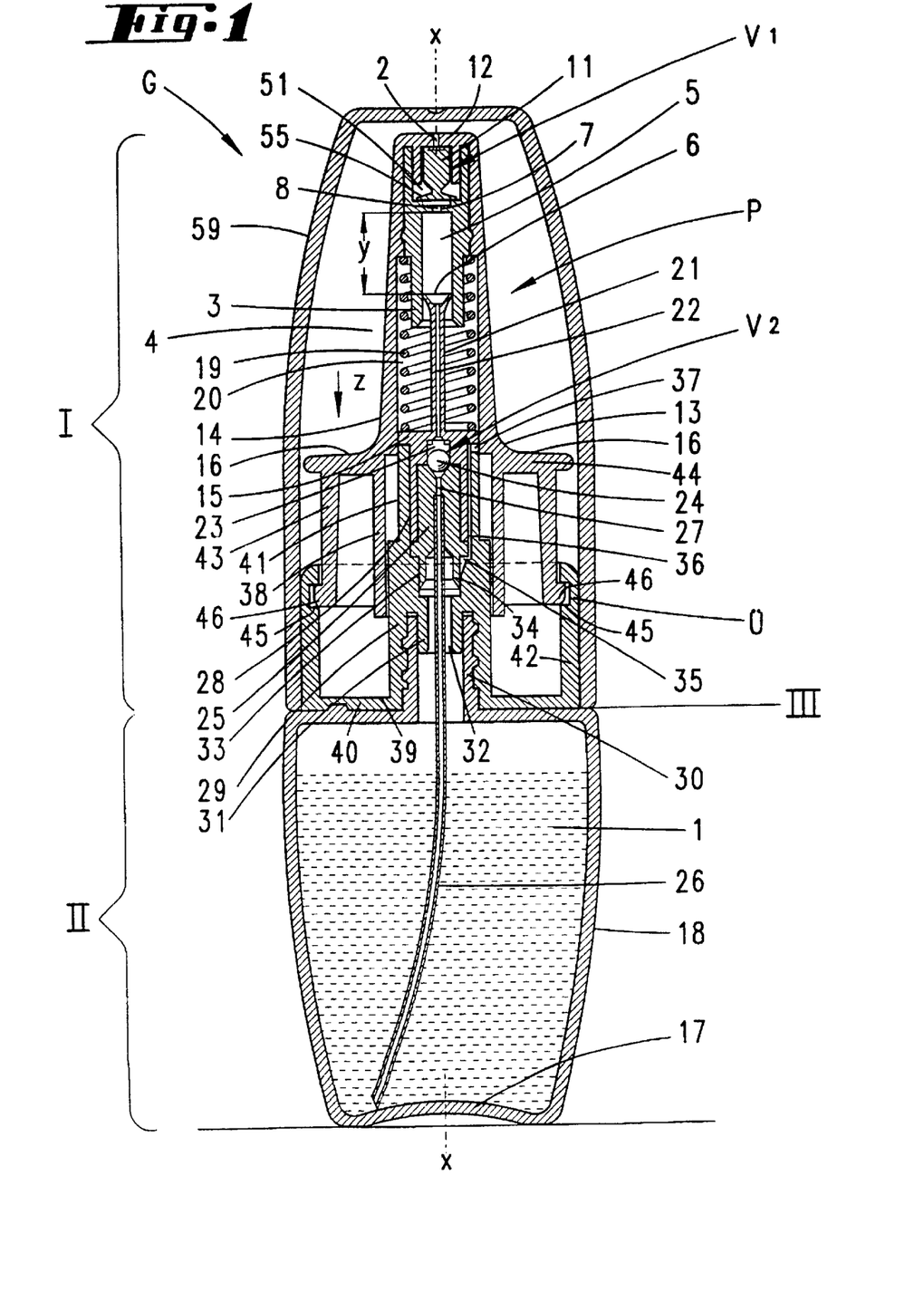
FIG. 1 shows the device according to the first exemplary embodiment in vertical section and provided with a protective cap.

According to the first exemplary embodiment, the valve body 11 of the outlet valve V1 is in the form of a separate component. It extends in the axial direction from the top side of the transverse wall 7 or valve-seating surface 10 to the underside of a top 12 which has the mouthpiece aperture 2.

In the exemplary embodiment shown, the top 12 is part of a handle of the device G, said handle forming a counter support 13. Starting from the top 12, the handle, which is developed to form a plug or spout, merges into a tubular stepped section 14. The upper end of the cylinder 3 is inserted and latched securely into that part of the said section which has a smaller inside diameter. The lower end of the said cylinder 3 projects freely into that part of the section 14 which has a somewhat larger inside diameter. At the lower end of the cylinder 3, the latter has an axial length which corresponds at least to the travel y for the pump actuation.

There is in addition a length section which encompasses the upper end region of a valve housing 15 of a second valve, functioning as inlet valve V2. Approximately at the level of the valve housing 15 inserted in section 14, the tubular section 14 or counter support 13 merges into a significantly widened portion. This creates essentially horizontally aligned shoulders 16. The index and middle fingers, for example, of an operating hand can be laid on these, while the thumb is placed against the underside of a bottom 17 of a docked liquid reservoir 18 in order to execute the relative motion between the cylinder 3 and the piston 6 of the pump P.

This pumping, which effects the dispensing of the liquid 1, takes place counter to the restoring force of a spring 19. Accordingly, the piston 6 and the cylinder 3 are spring-loaded in the direction of an enlargement in the volume of the pump chamber 5. The spring concerned is a helical compression spring. It has an essentially cylindrical winding and, according to the first exemplary embodiment, is placed on the freely projecting section of the cylinder 3. To this extent, the interior of the tubular section 14 forms a spring chamber 20. The upper winding at the end of the spring 19 is supported against the upper cross-sectional jump of section 14; the lower winding at the end of the spring 19 receives its support on the top side of the inserted section of the valve housing 15.

The piston stem 21 emanates from the upper section of the valve housing 15. The said piston stem is formed integrally and, by virtue of a cutout which passes all the way through it axially, is configured as an intake passage 22. This passage connects the pump chamber 5 on the reservoir side to a valve chamber 23. The latter accommodates, at the lower end of the pump P, the second valve, i.e. that forming what is referred to as inlet valve V1. This comprises a ball. Its funnel-shaped valve-seating surface, which is situated on the bottom side, bears the reference 24. It is part of a support 25, inserted from below into the valve housing 15, for a riser 26 associated with it by being plugged in. This riser extends as far as the bottom 17 of the liquid reservoir 18. The upper end of the said riser 26 is seated in a matching socket in the support 25, the insertion of the riser being limited by a stop. A central hole 27 corresponding to the internal cross-section of the riser starts above the corresponding internal stop. This hole establishes the flow connection with the valve chamber 23.

The valve housing 15 and the support 25 inserted into it from below are situated in an essentially cylindrical insertion cavity 28 in a central connecting stub 29.

The central connecting stub 29 serves as the pump's docking means for a threaded neck 30—representing the reservoir's docking means—of the liquid reservoir 18, which is of flask-shaped configuration. The reservoir-side end region of the connecting stub 29 can thus be compared with a screw cap; it has an appropriate internal thread and can carry a sealing ring on the top side. A snap-in catch which overlaps the joint, as drawn, can serve to prevent rotation.

A projection 31 projects into the upper end section of the threaded neck 30 and makes sealing contact at the periphery. This projection is hollowed out axially and leaves an annular gap 32 with respect to the outer wall of the riser 26, which is formed by a hose or the like.

The annular gap 32 continues in the direction of the mouthpiece aperture 2 into a cylindrical cutout 33. This adjoins coaxially and receives the lower end of the support 25, which there has a stepped cavity.

The lower end of the support 25 ends in a rotationally symmetrical tip on the reservoir side. The lip 34 created in this way is supported in a sealing manner on the surrounding wall of the cylindrical recess 33.

The said lip 34 is at an axial distance from the step between the annular gap 32 and cutout 33. A pressure balance path 35 starts above the lip 34. This path leads to the outside, i.e. is connected to atmosphere. This is achieved by means of a vertical passage 36 at the outer-wall end in the cylindrical section of the valve housing 15 and a radial passage 37 at the level of inlet valve V2. This radial passage opens below the inserted section of the valve housing 15, the opening being created either by clearance or a chamfer.

Here, section 14 merges into a third cross-section with a larger inside diameter formed on a cup-shaped part 38 with an appropriate wall offset acting as a guide on the outer wall of the connecting stub 29, (38) beginning just below the shoulders 16.

Figure 2:
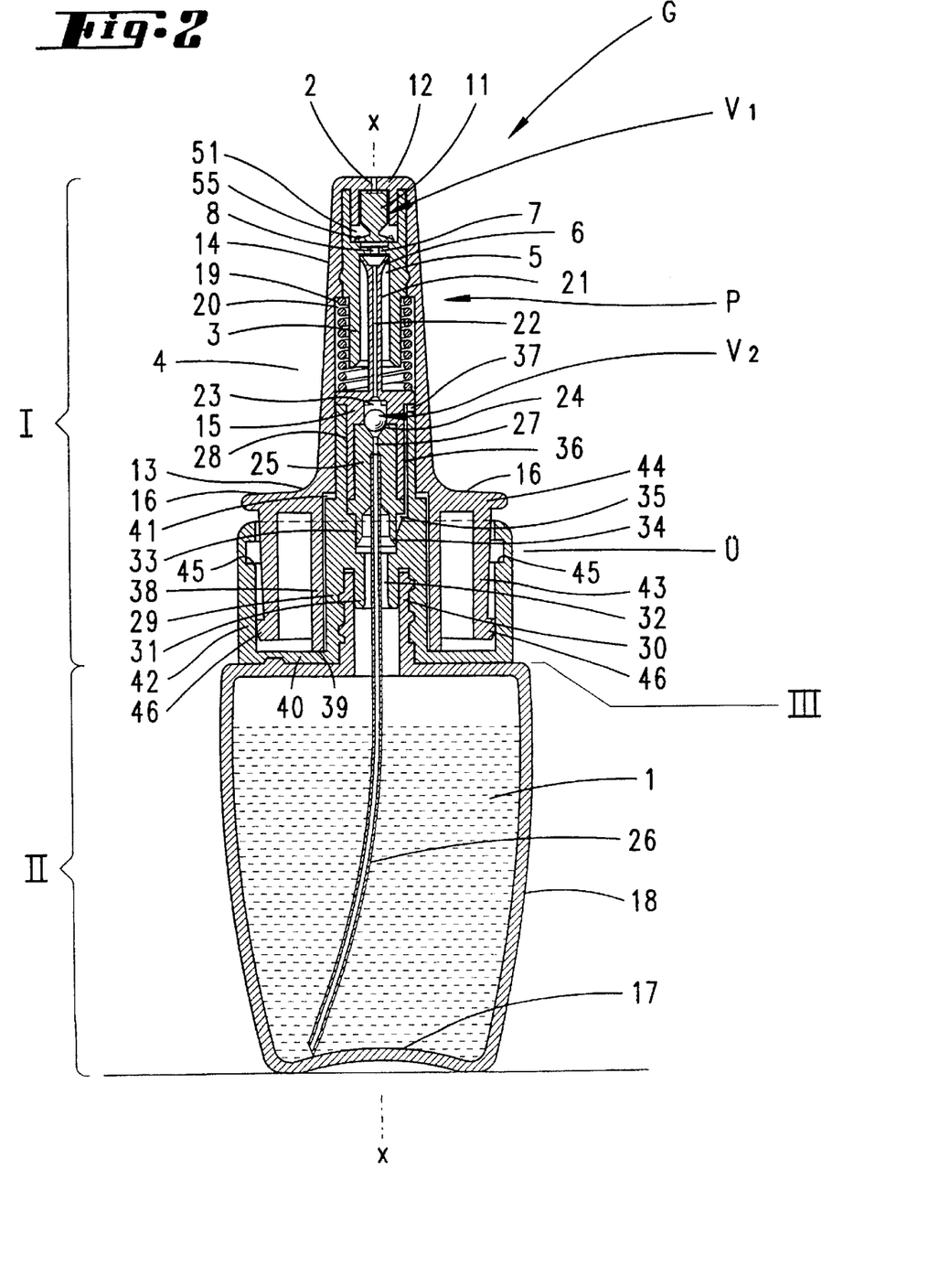
FIG. 2 shows the device in the same sectional view in the actuated state.

As can be seen from FIG. 2, the lower front edge of the cup-shaped part 38 forms a limiting stop with a counter stop 39 formed by the corresponding section of a continuation 40 of the connecting stub 29 in the form of the rim of a hat, It is the upper side which serves as the stop-forming element.

To receive the section 14 having a medium inside cross-sectional dimension, the upper end, which projects into the spring chamber 20, is continued with an appropriate cross-section, so that the section of smaller cross-section can run over the connecting stub 29. The corresponding reduction in cross-section on 29 is denoted by 41.

The continuation 40 in the form of the rim of a hat merges into an upward-pointing annular wall 42. Guided in this is an internal wall 43. This is connected to a cover-like portion 44 in the region below the shoulders 16 of the counter support 13 and expediently forms a continuous encircling wall.

The annular wall 42 and the wall 43 are used to form an overload threshold U. The latter comprises a retaining flank 45 formed by the continuation-side flank of a horizontally oriented groove on the inside of the annular wall 42. Supported in the region of the inner edge of this retaining flank 45 is a section of a rib 46 which is chamfered or has a transversely convex rounded shape. The rib 46 is formed on the outside of the wall 43 so as to be suitable for partial entry into the horizontal groove.

When the device G is actuated by the exertion of a force in the direction of arrow z, the resistance presented by the overload threshold Ü is overcome only above a certain exerted pressure load. This force is counter to the significantly lower restoring spring force of the spring 19 which always moves the pump P back into its initial position and holds it there when the pressure load is removed. Triggering is therefore possible only by deliberate effort. As soon as the chamfered or slightly rounded edge loses its grip at the retaining flank 45, the entire stored force is available for the corresponding pump actuation.

The mating flanks of the rib 46 and the groove are both perpendicular to the direction of actuation of the pump and have an irreversible locking effect. The spring force at least cannot break the components apart. The device G is held together after assembly by the mating flanks and they also provide a limiting stop for the opening stroke of the pump P.

The precisely apportioned quantity present in the pump chamber 5 from a preceding actuating stroke, as an initially solid jet of liquid, is atomized via the mouthpiece aperture 2 into a spray cone. The ultrafine particles are dispensed in a well-distributed manner at the target location.

Furthermore, the special configuration of the insert 11, which also fulfils another function, contributes to the production of the desired powerful jet which emerges. To this end, the method adopted is that the insert 11 or outlet valve V1, said insert being connected directly to or resting directly against the rear of the top 12 and being on the rear side of the mouthpiece aperture 2, the jet of liquid is deflected several times on this insert 11 in the region where it is formed, as a result of transverse channels 47 on the top side. A total of three such transverse channels 47 are formed. They are distributed at uniform angles and meet at the center, combining there. However, they do not meet centrically there but slightly eccentrically, forming a central swirl chamber 48 immediately underneath the mouthpiece aperture 2. The inside diameter of the swirl chamber 48 is somewhat larger than the hole cross-section of the mouthpiece aperture. As can be seen, the outer flanks of the shaft-like transverse channels 47, said flanks being set further out from the center, run tangentially into the circular wall sections of the swirl chamber 48, said wall sections being of essentially cylindrical design. What occurs there is virtually swirling in the form of a rod comparable with a wind spout, and hence swirling emergence of the liquid jet.

The transverse channels 47 and the swirl chamber 48 take the form of depressions in the end 11' of the insert 11. The inside of the top 12 closes this flow system, thus acting like a channel cover.

Figure 3:
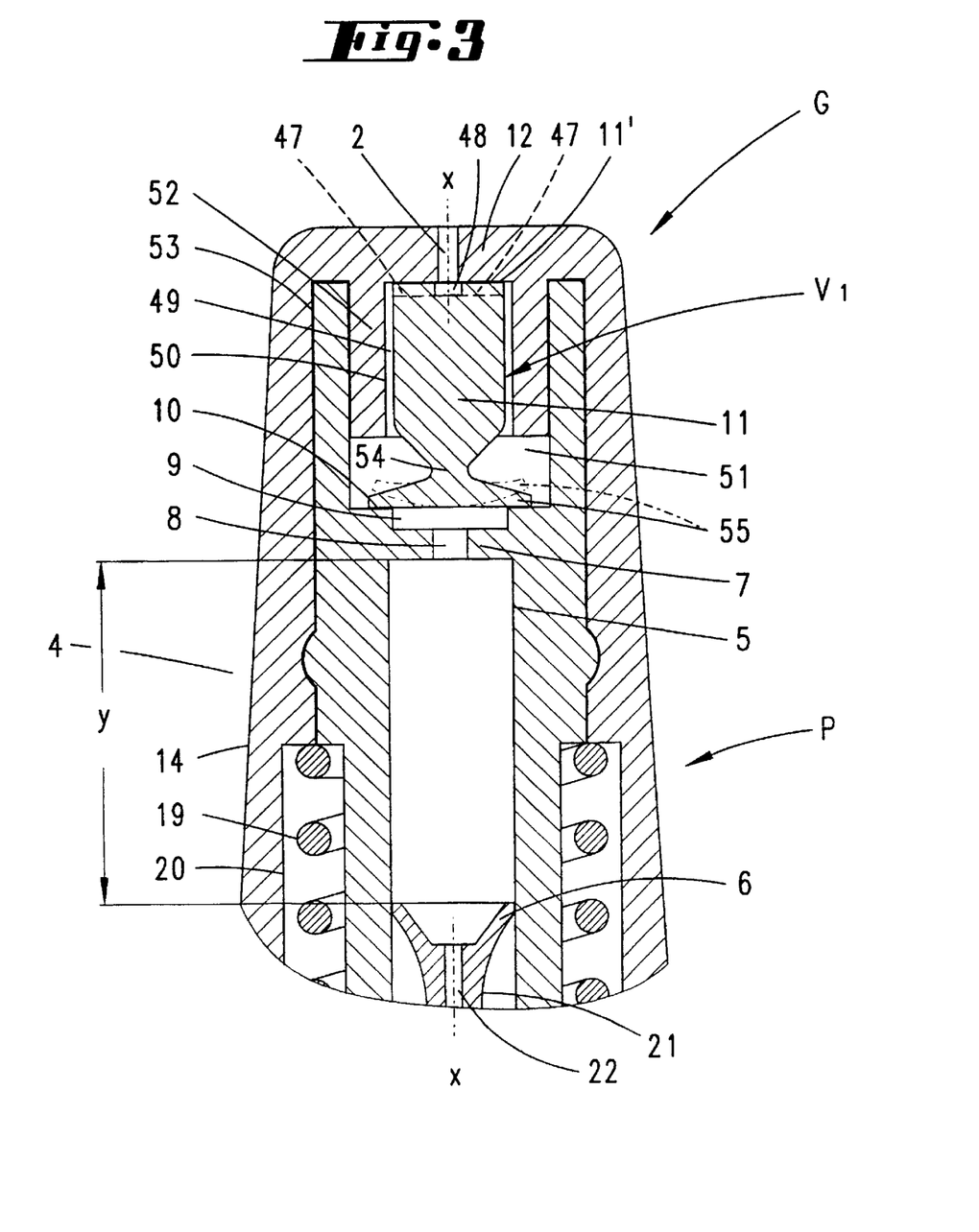
FIG. 3 shows an exert from FIG. 2 at the end where the mouthpiece aperture is located, the exert being further enlarged relative to the said figure and illustrating in chain-dotted lines, the valve function of the insert.

The entire surrounding area is used for the peripheral feeding of the apertures or ports of the transverse channels 47 emerging in the outer wall of the cylindrical section of the insert 11, in that the cylindrical section of the said insert 11 leaves a passage 49 in the form of an annular gap relative to the corresponding cylindrical inner wall 50 of the valve chamber 51 at that location. This results in an encircling catchment area which is of uniform priority all the way round in a symmetrical fashion. In the exemplary embodiment illustrated, in accordance with FIG. 3, the inner wall 50 mentioned is achieved by means of a sleeve 52 which starts from the top 12 and is formed on directly. This sleeve extends over the entire axial length of the cylindrical section of the insert 11. The freely projecting form of the sleeve 52 produces an annular well 53 in the mouth-side end region of the tubular section 14, the free end of which in practice forms the dispensing spout.

Figure 4:
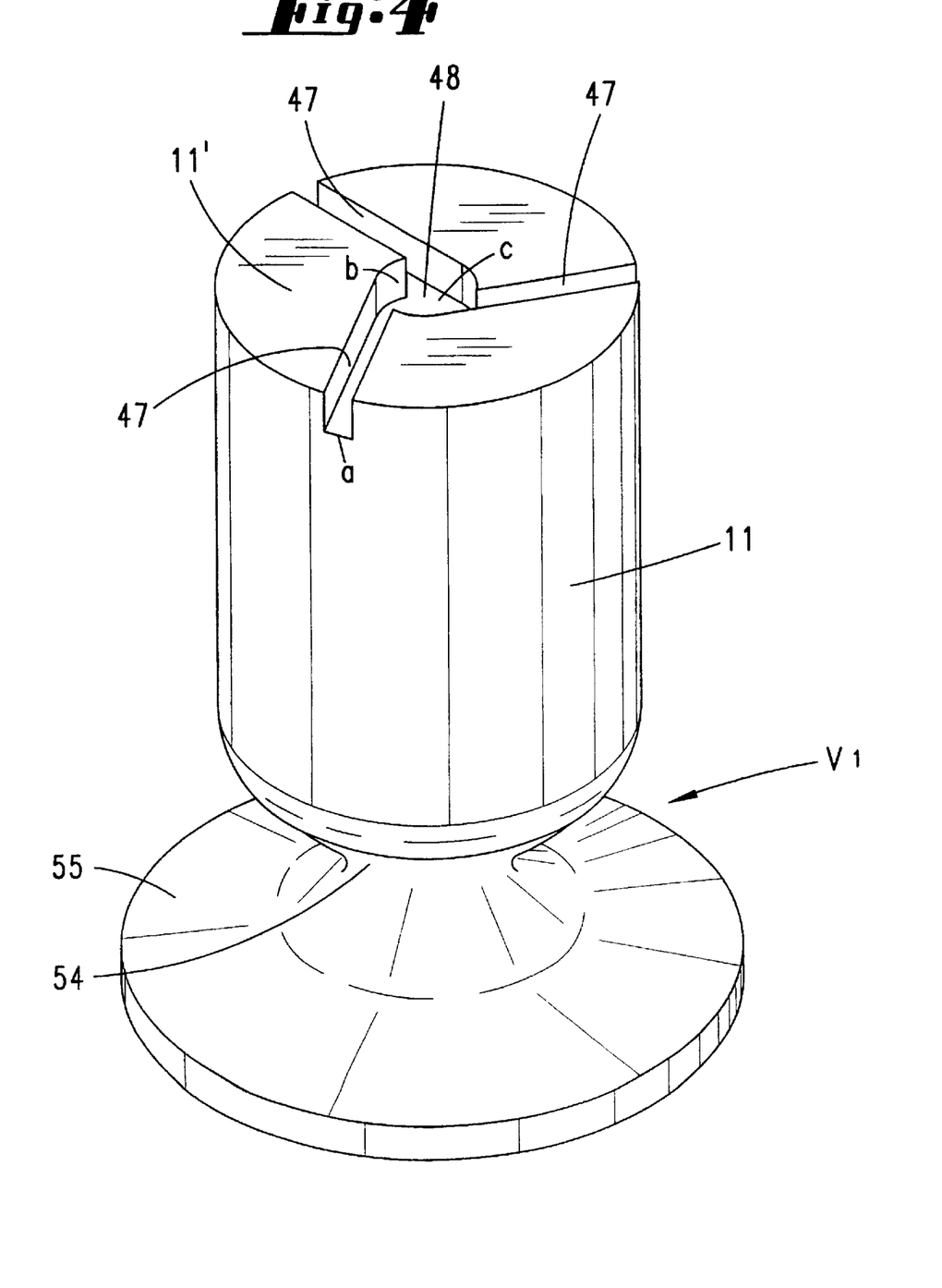
FIG. 4 shows the insert in isolated perspective representation, illustrating the top-side transverse-channel system, in further enlarged representation relative to FIG. 3.

As can be seen especially from FIGS. 2 and 4, the insert 11 has there a shape corresponding to a drinking glass with a foot. Thus, there is a stem 54 corresponding to a necked portion in the form of a wasp waist. A foot plate 55 starts from this stem 54. The said foot plate here forms the valve body. The foot plate 55 can be bent up elastically in the edge region, namely out of its otherwise flat extension. This valve open position is represented in chain-dotted lines in FIG. 3. There, the said edge region, which tapers peripherally to form a lip, rises from the corresponding valve-seating surface 10 if an excess pressure arises in the pump chamber 5. The medium can flow. It swirls in the region left free. However, the valve chamber 51 at that location could also be further enclosed by wall material, thus preventing virtually any undispensed residual liquid from collecting there.

The device G in accordance with the second exemplary embodiment (FIG. 5) is modified as regards the insert 11 such that this insert 11 now no longer occurs as a separate component but is formed integrally with a component which forms the device. Nevertheless, here too it functions as a filling piece which prevents the formation of significant residual quantities in the dispensing region. In concrete terms, this means that the insert 11 is here held by means of a cantilever 56. The arm-like cantilever is the bridging piece to a wall 57 of the pump cylinder 3, said wall being extended in the direction of the mouthpiece aperture 2. The cantilever extends radially.

Figure 5:
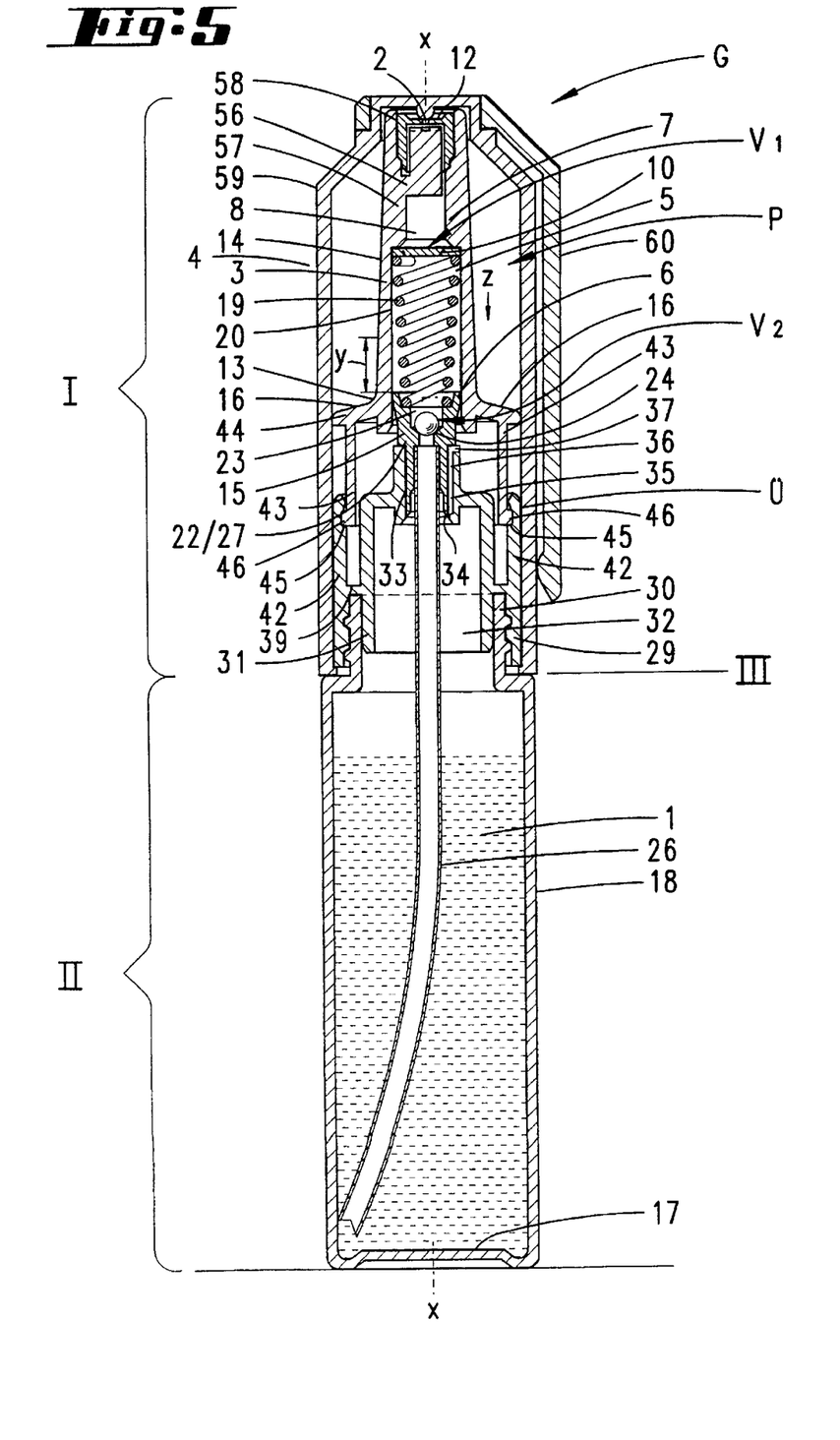
FIG. 5 shows the device in accordance with the second exemplary embodiment, again provided with a protective cap, i.e. in the initial position, also in vertical section.
Figure 6:
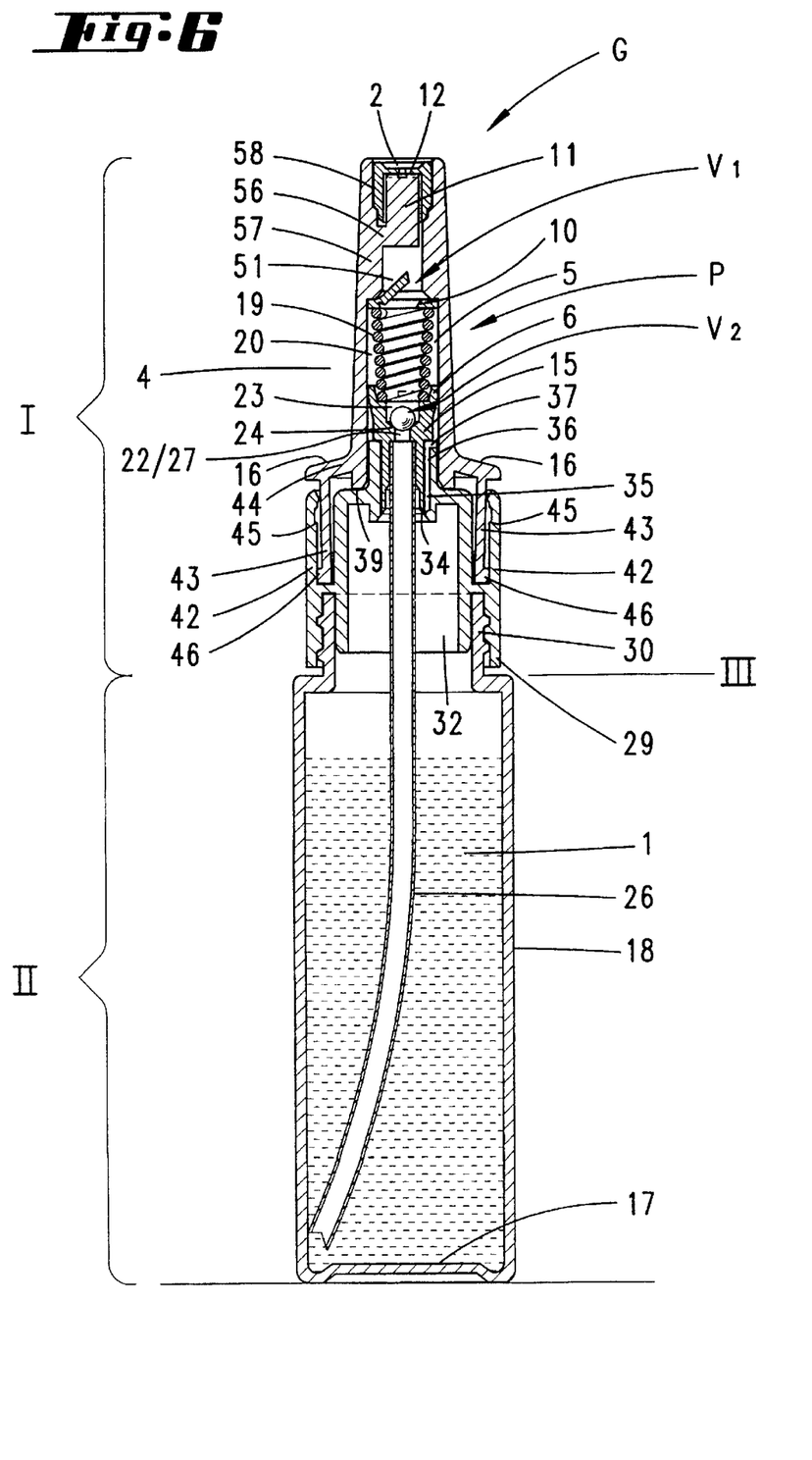
FIG. 6 shows this device in the actuated state, likewise in section.
Figure 7:
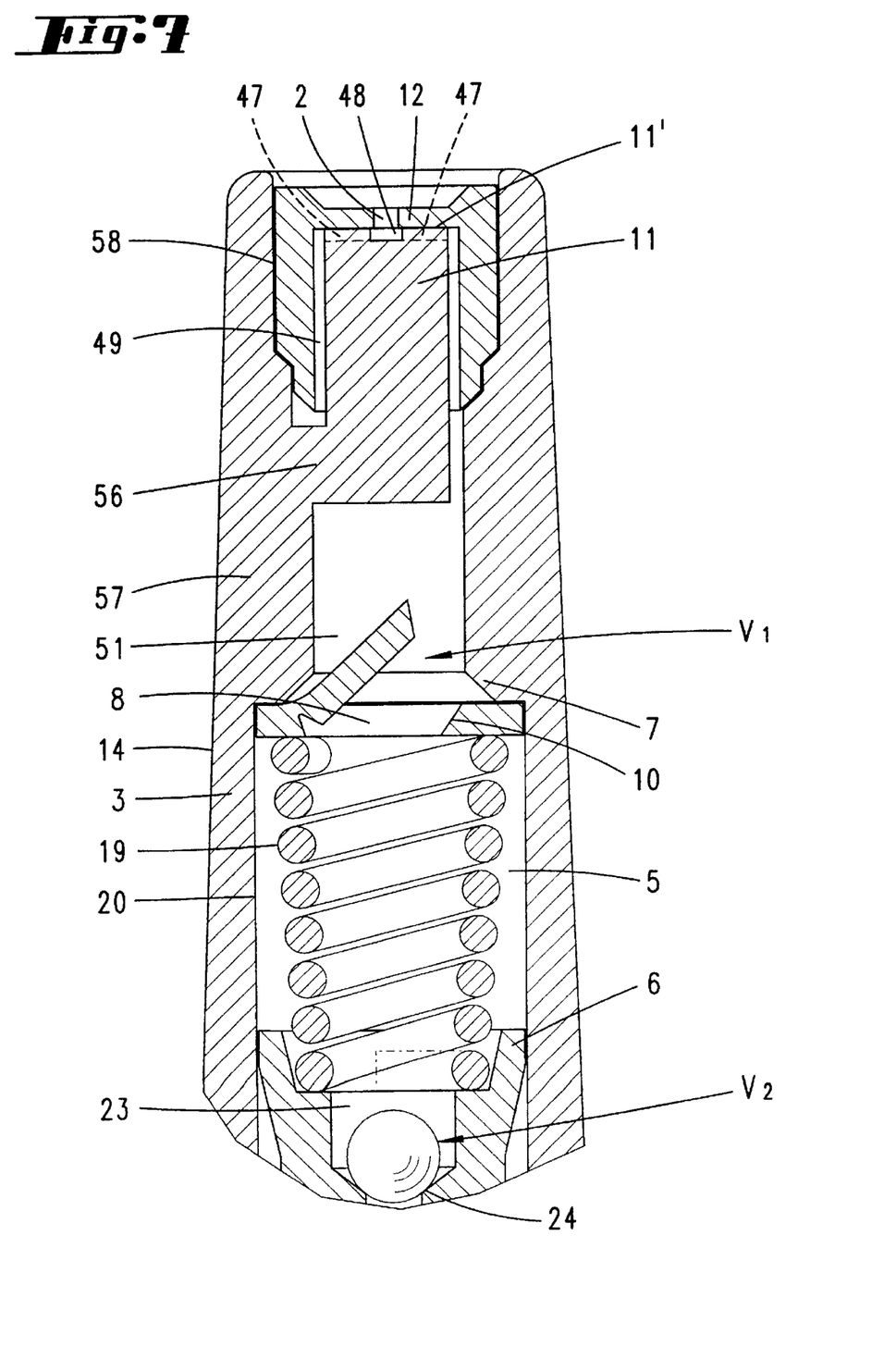
FIG. 7 shows an enlargement at the end where the mouthpiece aperture is located, as an exert from FIG. 6.
Figure 8:
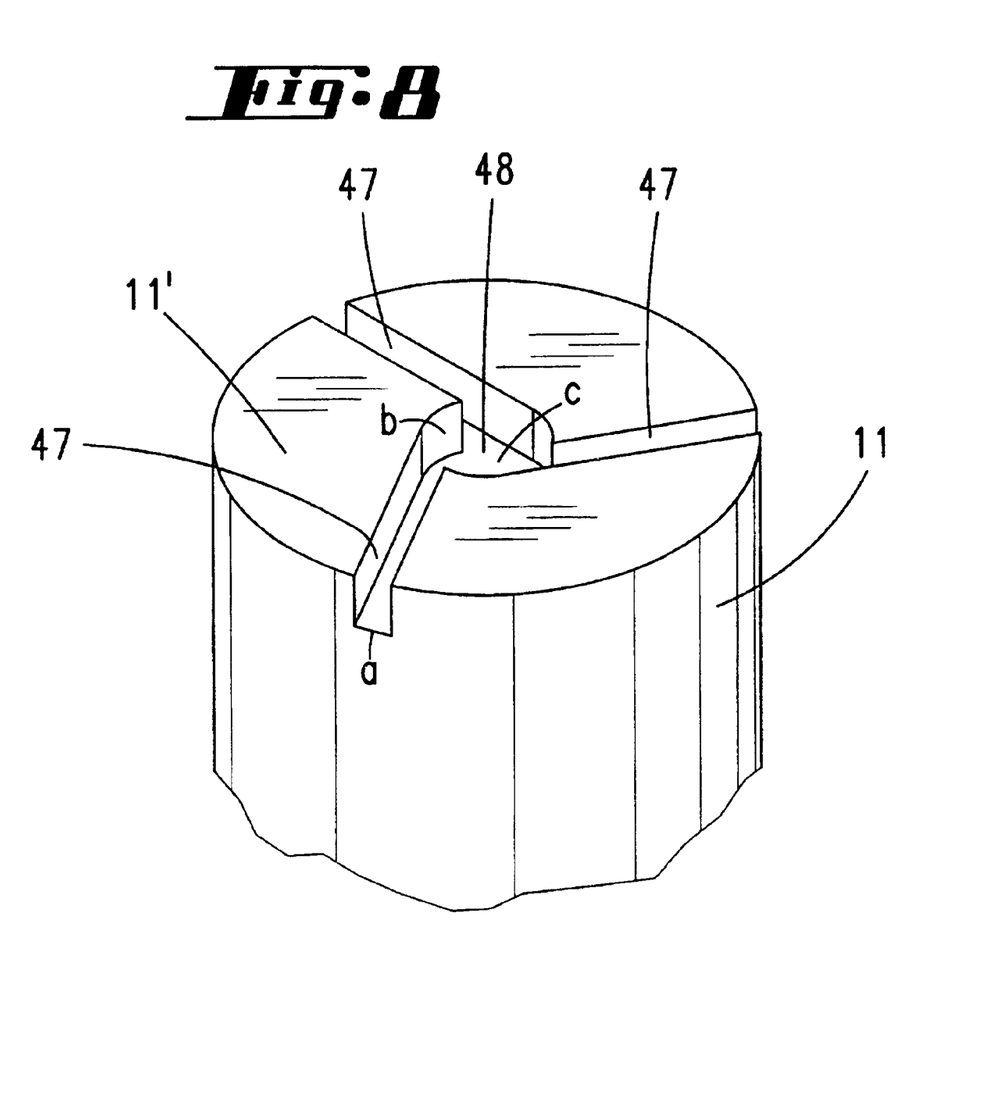
FIG. 8 shows the insert connected to the wall of the pump cylinder by way of a cantilever, likewise in perspective representation and considerably enlarged.

Moreover, the top 12 and outlet aperture 2 are formed on a cup-shaped plug which is introduced upside down into an axially oriented insertion socket 58 in the wall 57. Here too, however, the insert 11 which deflects the jet of liquid several times by means of transverse channels 47 on the top side is present on the rear side of the top 12 containing the mouthpiece aperture 2. The reference numerals are used analogously. The individual deflection points are denoted by a, b and c. Deflection point a forms the inlet opening of the medium, b is the deflection point, provided by eccentric curved connections, of the channel flank at that point and, finally, c is the base region of the swirl chamber 48, said base region directing the flow into the axial dispensing direction.

Another modification is the manner of arrangement of the spring 19. This spring is now directly within the pump chamber 5. The inlet valve V2 explained above and formed by a ball is situated at the top of the riser 26, while the outlet valve V1 arranged downstream of the upper end winding of the spring 19 is designed as a traditional flutter valve with a corresponding deflection space underneath the fixed insert 11 at that point provided by the valve chamber 51 at that location.

In order to prevent the ball from emerging into the pump chamber 5, the free end of the lower end spring winding is bent radially inwards in the manner of a web, with the result that there is no passage corresponding to the diameter of the ball.

The docking means are similar and will not be described in detail again here. The other reference numerals which may be required for comprehension are also used analogously, in the majority of cases without repeated mention in the text.

In order to safeguard against unwanted dispensing by means of other means in addition, both devices G can have a protective cap 59 which fits over at least the dispensing mechanism, i.e. covers the region I. In the second exemplary embodiment, this protective cap is provided with a clip 60, allowing the device G there to be carried like a ballpoint pen etc. The other device G too does not go beyond the favored pocket-sized format.

The protective cap in accordance with the second exemplary embodiment is furthermore used to cover the outlet edge of the mouthpiece aperture 2.

As far as material is concerned, plastic is chosen, taking into account the existence of an elasticity/flexibility matched to the required function, in order to ensure, for example, that the lip 34 can operate like an inner-tube or collar-type valve.

Figure 9:
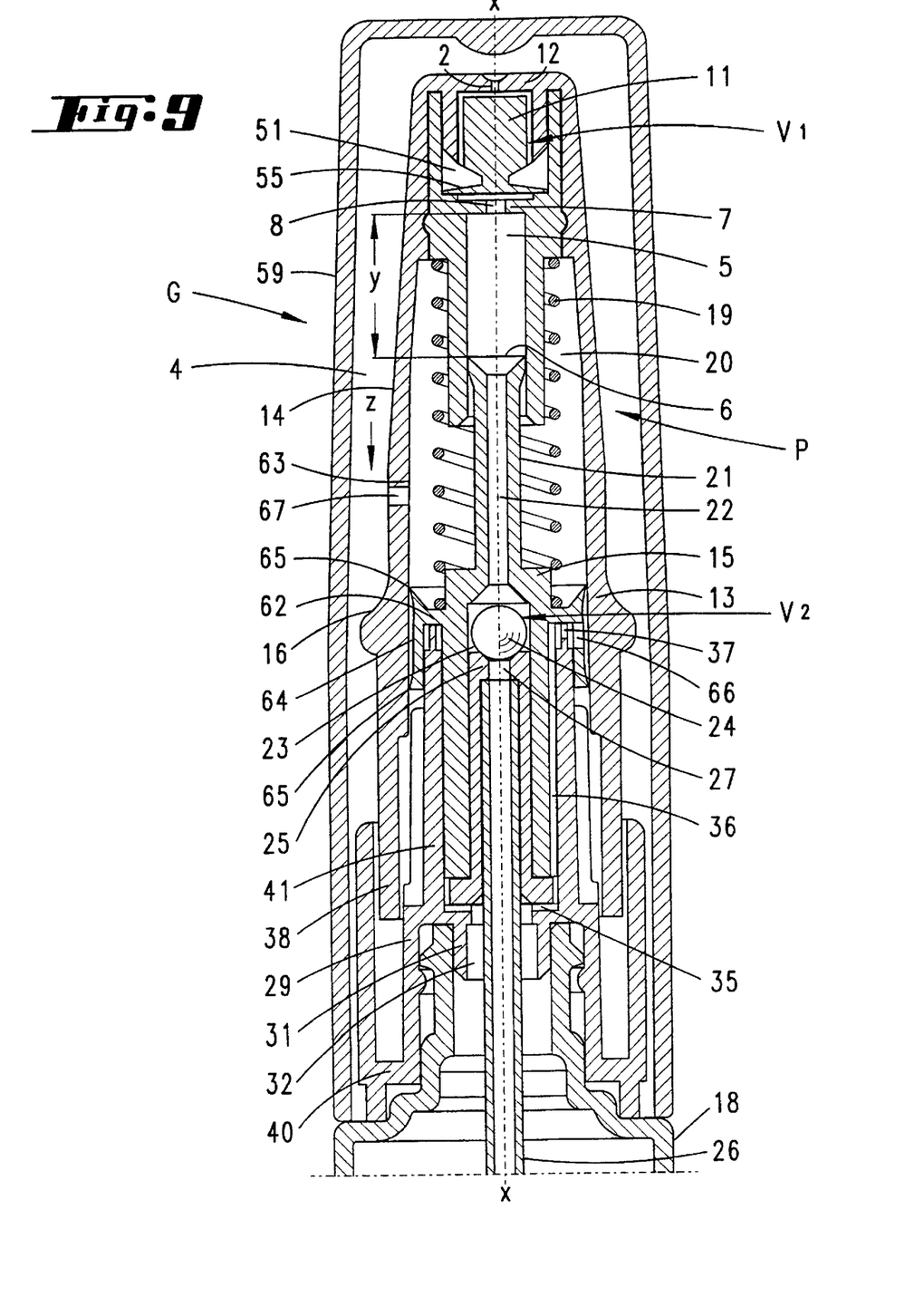
FIG. 9 shows a variant of the device according to the first exemplary embodiment in vertical section and provided with a protective cap, to be precise as a section through the narrow side of the device, which is configured to be flat in cross-section.
Figure 10:
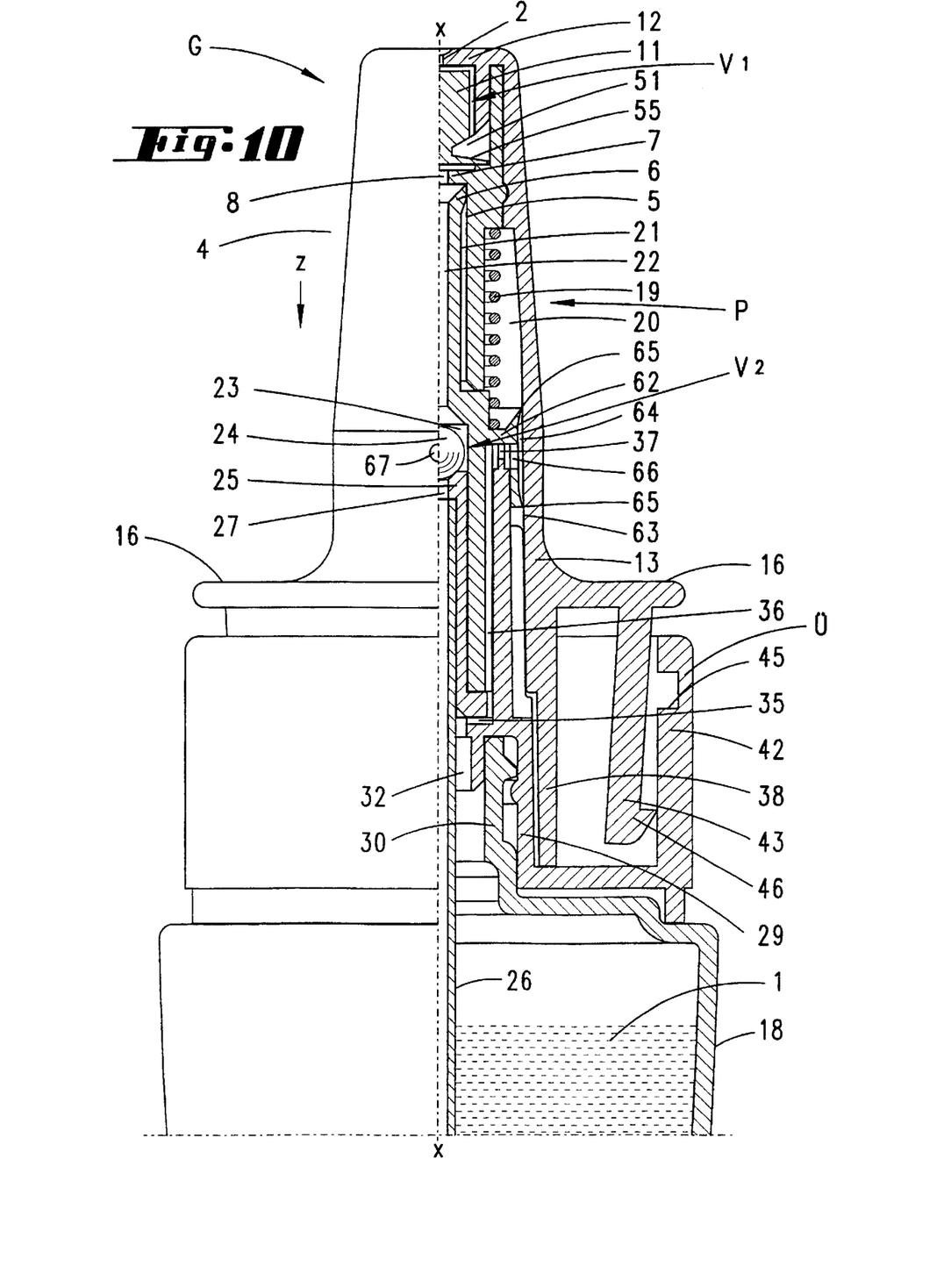
FIG. 10 shows a half-section through this device in the actuated position, as in FIG. 2.

The variant shown in FIGS. 9 and 10 differs in the design of the pressure balancing means. It can be seen that the use of the lip 34, described in the introduction, as the element which releases or controls the pressure balance path 35 has been dispensed with. It is replaced by a configuration which provides for the pressure balance path 35 to be controlled via a relative movement of the piston-cylinder device 4. For this purpose, the supply end of the piston stem 21 has a second piston 62 fixed on it.

The second piston 62 is guided on a cylindrical section of the inner wall of the spring chamber 20 of the handle of the device G, said inner wall functioning as cylinder 63.

The second piston 62 is of an axial length which corresponds approximately to its radius. The outer wall of the second piston 62 has a rotationally symmetrical annular depression between its two ends. This annular depression leaves an annular space 64 which extends towards the cylinder 63 and is closed at the ends. Sealing lips 65 which bear with a certain amount of prestressing are thus produced at the piston ends.

The pressure balance path 35 begins in the region of the captive end of the riser 26. In this variant, the initial section of the pressure balance path, said initial section being provided in this case by a radial-rib rim, likewise continues into the longitudinally running shaft 36. In the interior of the second piston, an air-flow connection to a radially directed hole 66 in the outer wall of the piston is then produced via the radial passage 37. This is the connection to the annular space 64.

In the initial position (FIG. 9), an air-passage opening 67 is located in the wall of the cylinder 63, above the second piston 62. This opening forms the connection to the atmosphere.

As is illustrated by comparing FIGS. 9 and 10, the hole 66 and air-passage opening 67 are offset at an angle. The air-passage opening 67, which provides a breathing opening as it were, is preferably located on the broad side of the device, that is to say remote from the shoulders 16 of the actuating part, these shoulders functioning as counter-support 13. It is thus not possible, in practice, for the air-passage opening 67 to be held closed.

On the transverse plane of the hole 66, the radial passage 37 may be surrounded on both sides by an annular chamber. The same applies as regards the foot of the holding device for the riser, this foot bearing on radial ribs. Said foot ends on the inner side of the shaft 36, that is to say on the shaft base.

In principle, the air balancing functions in the same way as has been described in relation to the basic version (FIG. 1). It should also be added that the quantity of composition located in the pump chamber 5 is dispensed with actuation of the handle counter to the restoring force of the spring 19, the air-passage opening 67 of the cylinder 63 being displaced into the surroundings of the outer surface of the second piston 62. The negative pressure, which is initiated as the quantity which has been separated off is dispensed, is thus dissipated by the hole 66, the shaft 36 and the initial section of the pressure balancing path 35. Prior to the corresponding lifting movement, the air located in the spring chamber 20 can escape via the air-passage opening 67 without excess pressure being produced. Excess pressure is thus not produced in the rear of the pump piston 6 either.

The references of the basis version are used analogously, in some cases without the text being repeated.

All the features disclosed are essential to the invention. The contents of the disclosure of the associated/attached priority documents (copy of the prior application) are herewith also incorporated in full into the disclosure of the application, with the purpose also of incorporating features of these documents into claims of the present invention.

What is claimed is:

1. Device (G) for dispensing liquids (1), especially medicinal liquids, from a mouthpiece aperture (2), the device comprising a piston-cylinder device operative as a pump, and threshold means;

wherein the mouthpiece aperture is connected to a supply of liquid, by manual actuation of the piston-cylinder device (4) which allows the manual actuation only after an overload threshold has been exceeded, there being a restoring spring force assigned to the overload threshold; and wherein the piston-cylinder device defines a pump chamber, and said spring force is provided by a spring disposed outside the pump chamber for returning a pump piston of the piston-cylinder device to its position relative to a pump cylinder of the piston-cylinder device upon completion of the manual actuation; and wherein said threshold means operatively interconnects between said piston and said cylinder to establish said overload threshold.

2. Device according to claim 1, further comprising:

a liquid reservoir with a riser, and an insert (11) on a rear side of the mouthpiece aperture, the rear side being upstream of the mouthpiece aperture with respect to a direction of flow of liquid through the aperture; and channels (47) located on a top side of the mouthpiece aperture and extending transversely of a direction of fluid flow, the top side being downstream of the mouthpiece aperture;

wherein the pump piston (6), which is connected by means of the riser (26) to the liquid reservoir (18) and is configured as an intake passage (22), is configured as a component which is fixed relative to the liquid reservoir (18), the pump cylinder (5), which is spring-loaded in the restoring direction, has at its free end the mouthpiece aperture (2), on the rear side of which is located the insert (11) for deflecting a jet of liquid several times by means of the transverse channels.

3. Device according to claim 2, further comprising a swirl chamber (48) on the rear side of the mouthpiece aperture, wherein the transverse channels (47) are arranged on the top side (11') of the cylindrical insert (11), around which liquid can flow, and are aligned slightly eccentrically, forming the central swirl chamber (48).

4. Device according to claim 2, wherein the pump cylinder comprises a wall (57) having a cantilever (56), and the insert (11) is held by the cantilever (56) of the wall (57) of the pump cylinder (3), the wall (57) of the pump cylinder being extended in a direction of the mouthpiece aperture (2).

5. Device according to claim 2, further comprising an actuating device, and a pressure balance path (35) located between the liquid reservoir (18) and the actuating device of the device (G).

6. Device according to claim 5, wherein the pressure balance path (35) is controlled by a lip (34) which rises under negative pressure.

7. Device according to claim 5, wherein the pressure balance path (35) is controlled via a relative movement of the piston-cylinder device (4).

8. Device (G) for dispensing liquids (1), especially medicinal liquids from a mouthpiece aperture (2), the device comprising a piston-cylinder device operative as a pump, and threshold means;

wherein the mouthpiece aperture is connected to a supply of liquid, by manual actuation of the piston-cylinder device (4) which allows the manual actuation only after an overload threshold has been exceeded, there being a restoring spring force assigned to the overload threshold; and the piston-cylinder device defines a pump chamber, and said spring force is provided by a spring disposed outside the pump chamber for returning a pump piston of the piston-cylinder device to its position relative to a pump cylinder of the piston-cylinder device upon completion of the manual actuation; and said threshold means operatively interconnects between said piston and said cylinder to establish said overload threshold;

the device further comprises a liquid reservoir with a riser, and an insert (11) on a rear side of the mouthpiece aperture, the rear side being upstream of the mouthpiece aperture with respect to a direction of flow of liquid through the aperture; and channels (47) located on a top side of the mouthpiece aperture and extending transversely of a direction of fluid flow, the top side being downstream of the mouthpiece aperture;

the pump piston (6), which is connected by means of the riser (26) to the liquid reservoir (18) and is configured as an intake passage (22), is configured as a component which is fixed relative to the liquid reservoir (18), the pump cylinder (5), which is spring-loaded in the restoring direction, has at its free end the mouthpiece aperture (2), on the rear side of which is located the insert (11) for deflecting a jet of liquid several times by means of the transverse channels; and the insert (11) comprises a foot plate (55) which forms a valve body.

9. Device according to claim 8, wherein the foot plate (55) is flexible in an edge region configured as a flat extension.

10. Device (G) for dispensing liquids (1), especially medicinal liquids, from a mouthpiece aperture (2), the device comprising a piston-cylinder device operative as a pump, and threshold means;

wherein the mouthpiece aperture is connected to a supply of liquid, by manual actuation of the piston-cylinder device (4) which allows the manual actuation only after an overload threshold has been exceeded, there being a restoring spring force assigned to the overload threshold; and the piston-cylinder device defines a pump chamber, and said spring force is provided by a spring disposed outside the pump chamber for returning a pump piston of the piston-cylinder device to its position relative to a pump cylinder of the piston-cylinder device upon completion of the manual actuation; and said threshold means operatively interconnects between said piston and said cylinder to establish said overload threshold;

the device further comprises a liquid reservoir with a riser, and an insert (11) on a rear side of the mouthpiece aperture, the rear side being upstream of the mouthpiece aperture with respect to a direction of flow of liquid through the aperture; and channels (47) located on a top side of the mouthpiece aperture and extending transversely of a direction of fluid flow, the top side being downstream of the mouthpiece aperture;

the pump piston (6), which is connected by means of the riser (26) to the liquid reservoir (18) and is configured as an intake passage (22), is configured as a component which is fixed relative to the liquid reservoir (18), the pump cylinder (5), which is spring-loaded in the restoring direction, has at its free end the mouthpiece aperture (2), on the rear side of which is located the insert (11) for deflecting a jet of liquid several times by means of the transverse channels;

the device further comprises an actuating device, and a pressure balance path (35) located between the liquid reservoir (18) and the actuating device of the device (G); and a second piston (62) mounted to a shaft of the pump piston (6) for movement therewith, and a cylinder-side annular space (64) serving as a second chamber for receiving the second piston;

wherein the second piston (62), via a rear surface thereof and the cylinder-side annular space (64), connects to the pressure balance path (35), by way of a shaft (36) and a radial passage (37), a top surface of the second piston being manually displaced into the region of an air-passage opening (67) leading to the interior of a cap of the dispensing device.

11. Device according to claim 10, wherein the second piston (62) has a hole (66) which connects the annular space (64) and the radial passage (37).

12. A delivery device for the delivery of an atomised spray of a metered volume of liquid, in particular liquid containing medicament, comprising: a reservoir for holding liquid; and a manually-actuated pump assembly comprising first and second body parts one of which includes a delivery orifice and one of a piston or a cylinder, and the other of which body parts includes the other of a piston or a cylinder, the piston being slideably disposed within the cylinder and the piston and the cylinder together defining a pump chamber for containing the metered volume of liquid to be atomized, the pump chamber having an inlet communicatable with the reservoir and an outlet communicatable with the delivery orifice; wherein the first and the second body parts are relatively movable between a first position in which the pump chamber has a first volume and a second position in which the pump chamber has a second volume smaller than the first volume, such that on actuation of the pump assembly in moving the first and the second body parts from the first position to the second position, the metered volume of liquid in the pump chamber is atomised through the delivery orifice; and wherein the first and the second body parts include inter-engaging elements which provide a mechanical resistance of a predetermined threshold to actuation of the pump assembly, and a return spring is disposed outside the pump chamber for returning the first and the second body parts to the first position.

13. The delivery device of claim 12, wherein the pump assembly further comprises a valve at the outlet of the pump chamber for allowing liquid to pass only in the out direction of the outlet of the pump chamber.

14. The delivery device of claim 12, wherein the pump assembly further comprises an outlet element disposed to the rear side of the delivery orifice, wherein the surface of the outlet element disposed to the rear side of the delivery orifice includes a swirl chamber adjacent the delivery orifice and a plurality of channels leading into the same.

15. The delivery device of claim 14, wherein the plurality of channels are offset with respect to the center of the swirl chamber.

16. The delivery device of 14, wherein the outlet element includes a resilient plate which acts as the valve at the outlet of the pump chamber.

17. The delivery device according to claim 14, wherein the outlet element is attached to the one of the first and second body parts which includes the delivery orifice.

18. The delivery device according to claim 12, wherein the first body part includes the delivery orifice and the cylinder and the second body part includes the piston, the piston including a passageway through which liquid is in use drawn from the reservoir into the pump chamber.

19. The delivery device according to claim 12, wherein the first and second body parts are configured such that the pump chamber is substantially emptied on movement of the first and second body parts to the second position.

20. The delivery device according to claim 12, wherein the pump assembly includes a pressure balance path for the reservoir.

21. The delivery device of claim 20, wherein the pressure balance path includes a flap valve provided by a resilient lip which is opened with a reduced pressure in the reservoir.

22. The delivery device of claim 20, wherein the one of the first and the second body parts which includes the first mentioned cylinder includes a further cylinder having an opening in the peripheral wall thereof, and the other of the first and the second body parts which includes the firstmentioned piston includes a further piston, the further piston being slideably disposed within the further cylinder and including a recess in the peripheral surface thereof which is in communication with the reservoir, with the opening in the peripheral wall of the further cylinder being located so as in use to be brought into communication with the recess in the peripheral surface of the further cylinder and thereby provide a pressure balance path which is open when the first and the second body parts are in the second position.

23. The delivery device of claim 12, wherein the delivery device is a nasal delivery device.

* * * * *